United States Patent [19]
Akiyama et al.

[11] Patent Number: 5,402,797
[45] Date of Patent: Apr. 4, 1995

[54] APPARATUS FOR LEADING BRAIN WAVE FREQUENCY

[75] Inventors: Kazuhiro Akiyama; Satoshi Saitoh, both of Kawagoe, Japan

[73] Assignee: Pioneer Electronic Corporation, Tokyo, Japan

[21] Appl. No.: 207,682

[22] Filed: Mar. 9, 1994

[30] Foreign Application Priority Data

Mar. 11, 1993 [JP] Japan ................. 5-050917
Mar. 12, 1993 [JP] Japan ................. 5-052358
Dec. 24, 1993 [JP] Japan ................. 5-327824

[51] Int. Cl.$^6$ ................................. A61B 5/0482
[52] U.S. Cl. ................................. 128/732
[58] Field of Search ................. 128/731–732

[56] References Cited

U.S. PATENT DOCUMENTS

| 3,855,998 | 12/1974 | Hidalgo-Briceno | 128/732 |
|---|---|---|---|
| 3,875,930 | 4/1975 | Silva et al. | 128/732 |
| 3,967,616 | 7/1976 | Ross | 128/732 X |
| 4,984,578 | 1/1991 | Keppel et al. | 128/732 |
| 5,024,235 | 6/1991 | Ayers | 128/732 |
| 5,241,967 | 9/1993 | Yasushi et al. | 128/732 |

Primary Examiner—Angela D. Sykes
Attorney, Agent, or Firm—Sughrue, Mion, Zinn, Macpeak & Seas

[57] ABSTRACT

Disclosed is a brain wave leading apparatus which can achieve a high brain wave leading efficiency when a human brain wave frequency is led to a desired frequency band. This brain wave leading apparatus comprises a brain wave sensor for detecting the brain wave of a person to be tested (subject) during brain wave leading, and a control unit for renewing a leading center frequency for leading the brain wave frequency therewith. The brain wave frequency of the subject is measured even during brain wave leading, and based on a weighted mean frequency f' detected in a predetermined interval, a leading center frequency F in a subsequent interval is determined. The leading of the brain wave frequency is continued with the leading center frequency F supplied from the control unit. Even if the weighted mean frequency of the subject during leading varies, therefore, the leading center frequency follows up that change, so that brain wave leading will be executed in a short period of time.

8 Claims, 10 Drawing Sheets

APPARATUS FOR LEADING BRAIN WAVE FREQUENCY

BACKGROUND OF THE INVENTION

1. Field of the Invention

This invention relates to an apparatus for leading a physiological/psychological state of a person to a desired state, and, more particularly, to a brain wave frequency triggering apparatus which leads the brain wave of a person to a desired frequency band.

2. Description of the Related Art

It is known that brain wave of a human being have a close relation to his physiological/psychological state. When a person is in relaxed condition, alpha ($\alpha$) waves (about 8 to 13 Hz) appear most in the brain. Beta ($\beta$) waves (about 14 to 30 Hz) appears most when the person is in active condition, while theta ($\theta$) waves (about 4 to 7 Hz) appear most when the person feels sleepy.

A drawing phenomenon in which brain wave frequency is synchronized to external signal frequency is seen on brain waves of a human being. If an external signal is supplied to a person for leading current brain wave to a desired frequency band in which the corresponding brain wave frequency appears most, the person can be led to desired physiological/psychological state.

There is a brain wave frequency leading apparatus which supplies a stimulation such as light and/or sound to a person in order to trigger particular brain wave frequency corresponding to $\alpha$ waves in the brain to relax the person by utilizing those mutual effects of the brain wave frequency and the physiological/psychological state, thus reducing his mental stress or intending his mental concentration.

In this brain wave leading apparatus, a brain wave signal of a person to be tested (hereinafter referred to as "subject"), which is detected by a sensor, is passed through a filter to be converted to an optical signal, and then this optical signal is feedback to the subject to lead the brain wave. To lead the brain wave of the subject to a desired frequency band, a weighted mean frequency of the brain wave of the subject at rest or a weighted mean frequency $f_0$ at the time the brain wave is swept with a predetermined frequencies is obtained to compute a leading center frequency F suitable for brain wave leading, and the brain wave is triggered using only a signal included in a predetermined frequency band around this leading center frequency F.

In the above brain wave leading apparatus, however, the leading of the brain wave usually starts after the brain wave comes into an at-rest state or after the sweeping of the brain wave frequency is complete. If the brain wave frequency of the subject during brain wave leading becomes apart from the leading center frequency F, therefore, the brain wave leading efficiency tends to decrease. As a result, there are some cases which fail to lead the brain wave.

SUMMARY OF THE INVENTION

It is therefore an object of the present invention to provide a brain wave leading apparatus which achieves a high brain wave leading efficiency when brain wave of a person leads to a desired frequency band.

To achieve the above object, there is provided a brain wave leading apparatus for converting a brain wave signal of a subject to a biostimulation signal and supplying the biostimulation signal to the subject, thereby leading the brain wave frequency of the subject to a desired frequency band, which comprises detection means for detecting the brain wave signal of the subject during leading of the brain wave signal; and renewal means for renewing the biostimulation signal based on an output of the detection means.

In a brain wave leading apparatus according to the present invention, the brain wave signal of a subject is measured even during leading of the brain wave based on a biostimulation signal. The renewal means updates the biostimulation signal every predetermined interval based on the output of the detection means and then continues the leading of the brain wave signal by the renewed frequency. This apparatus of the invention therefore prevents an increasing of the difference between the frequency of the biostimulation signal for leading a brain wave signal and the current frequency of the brain wave signal of the subject.

As the brain wave frequency is led based on the biostimulation signal that is renewed at least a predetermined interval, the frequency of the biostimulation signal supplied to the subject can close up the brain wave frequency of the subject. It is therefore possible to efficiently trigger the desired brain wave frequency in the brain of the subject, thus improving the brain wave leading efficiency.

In a preferred embodiment of this invention, the biostimulation signal is changed based on the brain wave frequency detected during leading every predetermined interval. In another preferable operational mode, the biostimulation signal is renewed based on the result of comparison between the frequency of the biostimulation signal and a predetermined frequency band set around the frequency of the brain wave detected during leading. In a further preferable operational mode, the leading status of the brain wave is evaluated and the biostimulation signal then is changed based on the normalization of the evaluation result.

In a still further preferable operational mode, the brain wave leading apparatus includes light emitting means for leading the brain wave of the subject to a desired frequency band with an optical signal included in the biostimulation signal. The light emitting means includes means for emitting a first optical stimulation signal to be irradiated at a right field-of-view position of each eyeball, and a second optical stimulation signal, which is irradiated at a left field-of-view position of each eyeball and has a phase difference to the first optical stimulation signal. In this brain wave leading apparatus, optical stimulation signals of different phases are respectively irradiated at the right field-of-view position and left field-of-view position of each eyeball to independently stimulate the right and left hemispheres to activate both brain hemispheres. This structure of the embodiment further improves information exchange between the right and left hemispheres to lead the brain wave frequency of the subject to a desired frequency band. The phase difference between the first and second optical stimulation signals is preferably controlled to control the activation statuses of the right and left hemispheres.

DETAILED DESCRIPTION OF THE PREFERRED EMBODIMENTS

For better understanding of the above and other objects, the structure and advantages of the present invention, preferred embodiments of the present invention will now be described hereinafter referring to the accompanying drawings.

Figure 1:
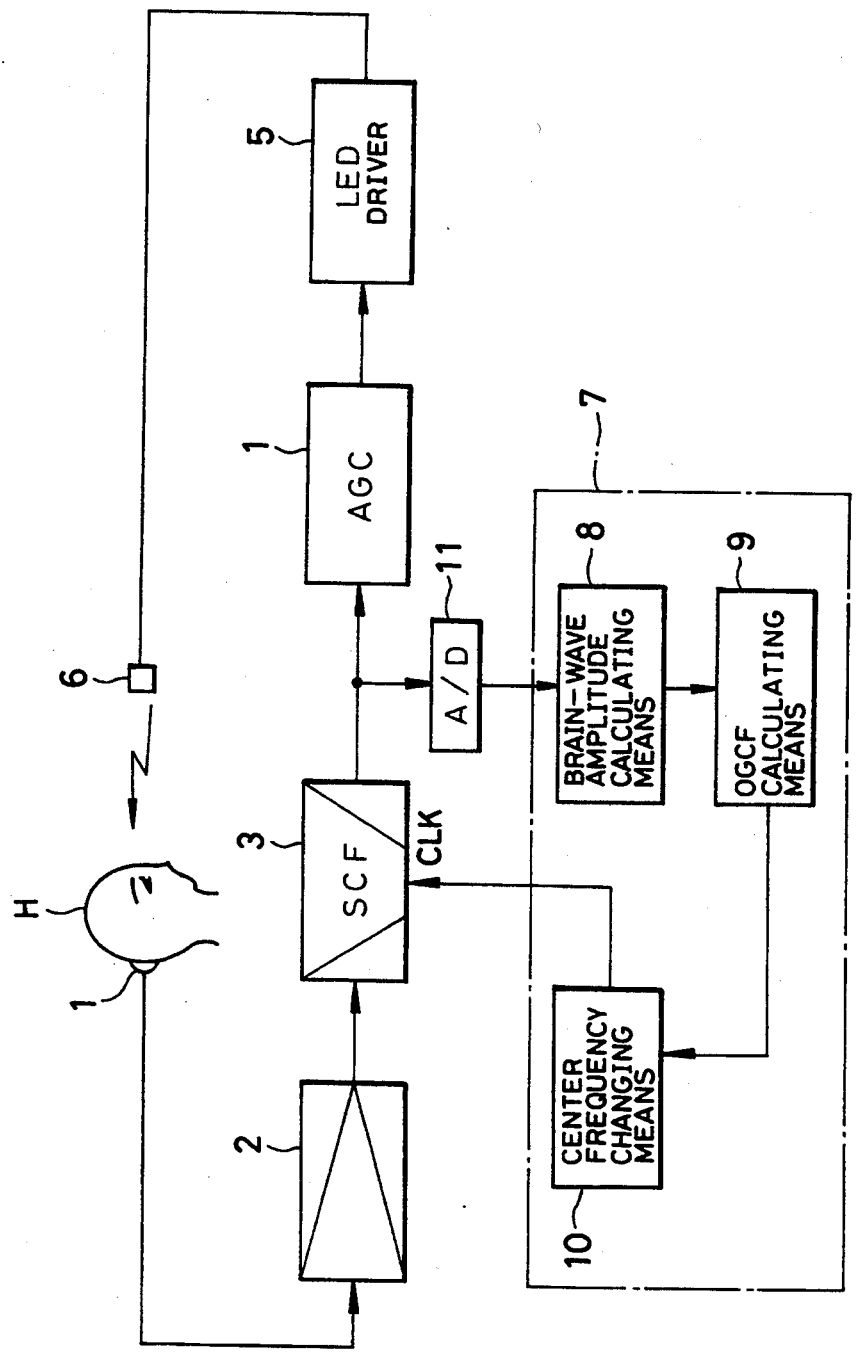
FIG. 1 is a diagram illustrating one embodiment of brain wave leading apparatus according to the present invention.

FIG. 1 shows one preferred embodiment of a brain wave leading apparatus according to the present invention. The brain wave leading apparatus of FIG. 1 comprises a brain wave sensor 1 which may be attached at a predetermined position of the head of a subject H and includes electrodes, a bioamplifier 2, a bandpass filter 3, an automatic gain controller (AGC) 4, a biostimulation driver 5, and stimulation means 6 for stimulating the subject H directly. This apparatus is controlled by control means 7.

The brain wave sensor 1 is detection means which detects the brain wave signals within the brain of the subject H. The bioamplifier 2 connected to the brain wave sensor 1 amplifies a brain wave signal detected by the brain wave sensor 1 to a proper signal level. The bandpass filter 3 is a variable band type connected to the bioamplifier 2, and is preferably a switched capacitor filter (SCF) which alters the band center frequency by changing the frequency of a clock CLK. The AGC 4, which is connected to the bandpass filter 3, automatically controls the brain wave signal passed through the bandpass filter to a certain level. The biostimulation driver 5, which is connected to the AGC 4, drives the stimulation means 6 connected to the biostimulation driver 5, with the signal supplied from the AGC 4. This stimulation means 6 preferably comprises one or more light emitting diodes (LED or LEDs), each of which is blinked by the biostimulation driver 5 respectively. Flickering light emitted by the LED is supplied to the subject H as a biostimulation signal for leading brain wave to a desired frequency band.

In this preferred embodiment, light is used as a biostimulation signal, a sound may be used instead of light as a biostimulation signal. Both light and a sound may also be used together. In case of using a sound as a biostimulation signal, the stimulation means 6 preferably includes a loudspeaker.

The control means 7 is preferably constituted of a microcomputer. The control means 7 includes brain wave amplitude calculating means 8, optimal leading center frequency (OGCF) calculating means 9 and center frequency changing means 10, each of which has a CPU (Central Processing Unit), a ROM (Read Only Memory), a RAM (Random Access Memory), etc. The center frequency changing means 10 alters the center frequency of the bandpass filter 3 by changing the frequency of the clock CLK. The brain wave amplitude calculating means 8 acquires the amplitude level of a sweep center frequency of the brain wave signal passed through the bandpass filter 3. The OGCF calculating means 9 computes an optimal leading center frequency F for leading brain wave to a desired frequency band based on the amplitude level of each center frequency obtained by the brain wave amplitude calculating means 8. The OGCF calculating means 9 also controls the center frequency changing means 10 in such a way that the center frequency of the bandpass filter 3 becomes equal to the optimal leading center frequency F. Reference numeral "11" denotes an A/D converter for converting an analog signal to a digital signal.

There are several methods to operate the above brain wave leading apparatus, which will be discussed one by one below. The operational feature common to the each method lies in that brain wave frequencies of a subject are measured at least every predetermined interval during leading the brain wave frequency. Therefore, the leading center frequency F is renewed in accordance with the brain wave frequency measured at a predetermined interval during leading, and the leading of the brain wave frequency is continued based on the renewed leading center frequency F.

The first operation in the case of triggering $\alpha$ waves in the brain of the subject H will be described referring to FIGS. 2 and 3. In this operation, a weighted mean frequency f' of the brain wave during leading is measured even after the leading of the brain wave frequency has started, and the leading center frequency F is renewed based on the weighted mean frequency f' detected every renewal period. A specific process will be described below referring to FIG. 2.

Figure 2:
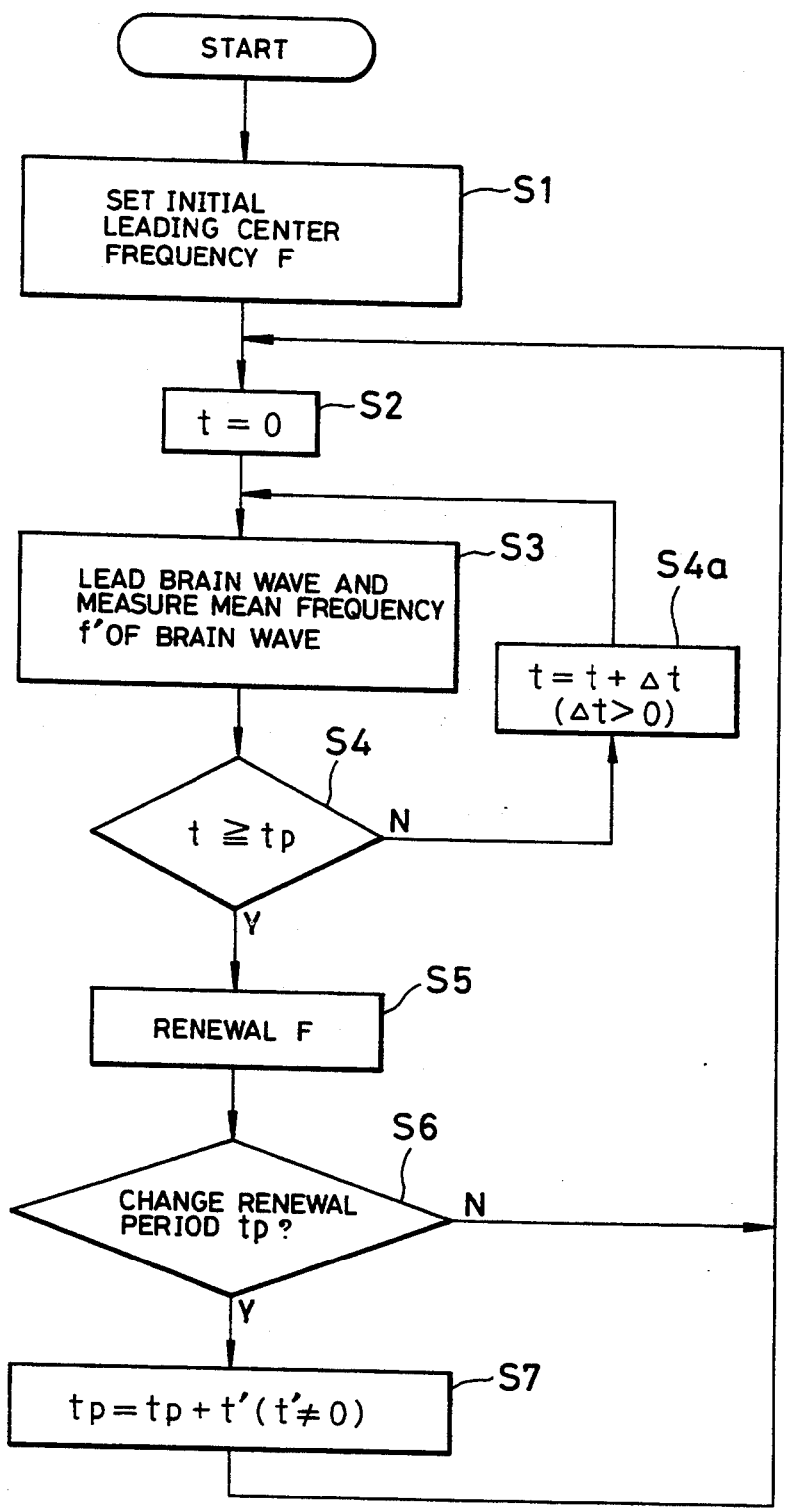
FIG. 2 is a flowchart illustrating one example of the operation of the brain wave leading apparatus shown in FIG. 1.
Figure 3:
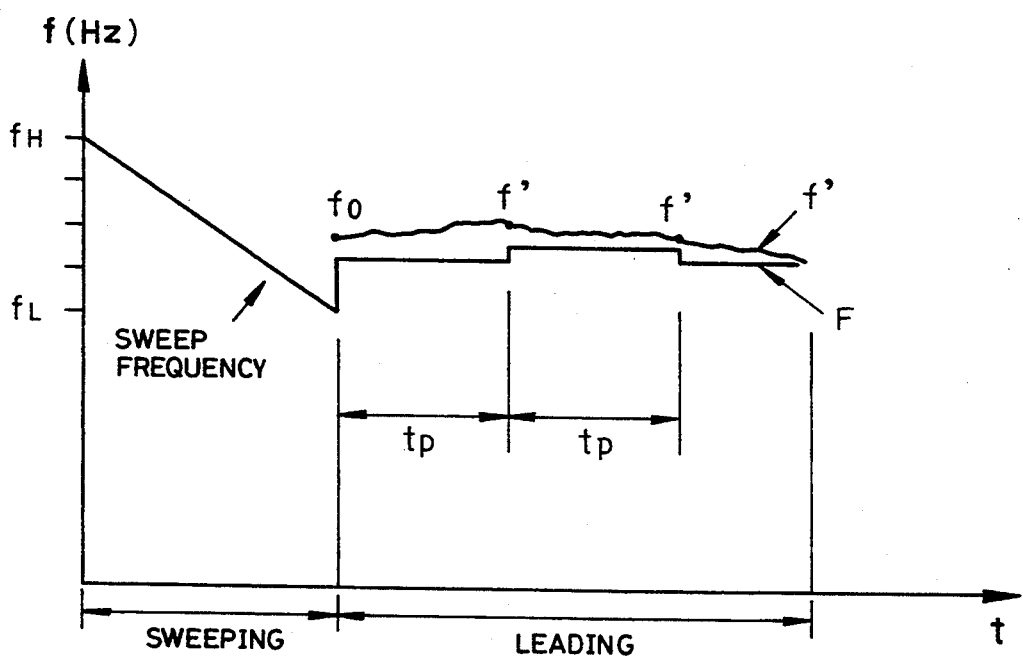
FIG. 3 is a diagram for explaining how to lead brain waves with the flowchart given in FIG. 2.

In FIG. 2, the initial leading center frequency F at the beginning of the leading is defined in step S1. The leading center frequency F at the beginning of the leading is preferably determined by a weighted mean frequency $f_0$ at the first stage of the leading, which is obtained through a sweeping operation before the leading starts.

In this sweeping operation, when a sweep start command is given, the center frequency changing means 10 sets the center frequency to an upper limit frequency $f_H$ of the frequency range, for example, 13 Hz, and then a clock which provides the center frequency f=13 Hz is sent to the bandpass filter 3. Accordingly, the sweep start frequency of the bandpass filter 3 is set to f=13 Hz as shown in FIG. 3. The brain wave amplitude calculating means 8 calculates the amplitude level at the sweep frequency f=13 Hz based on the brain wave signal supplied from the bandpass filter 3 at f=13 Hz. The calculating means 8 then saves the level in an internal memory of the control means 7. Then, the center frequency changing means 10 sequentially reduces the center frequency from $f_H=13$ Hz to a lower limit frequency $f_L=8$ Hz by a predetermined frequency $\Delta f$, and detects and saves the amplitude level of the frequency every time the center frequency is reduced by $\Delta f$. When the sweeping from $f_H=13$ Hz to $f_L=8$ Hz is complete, the OGCF calculating means 9 reads each sweep center frequency and its amplitude level stored in the brain wave amplitude calculating means 8, and computes a desired leading center frequency F most suitable for the leading of the brain wave, based on an equation (1) below.

$$F=(\Sigma A_i f_i / \Sigma A_i) \pm f_b \quad (1)$$

where $f_i$ is the i-th sweep center frequency, $A_i$ is the amplitude level of the i-th sweep center frequency, and
$f_b$ is a bias frequency.

In the equation (1), the first term on the right-hand side is a weighted mean frequency $f_0$ before leading in a swept frequency band ($f_H$-$f_L$), and the second term on the right-hand side is the bias frequency for efficiently leading the brain wave to a desired frequency band. While there is a entraining phenomenon on brain waves as mentioned above, brain wave leading will be accomplished efficiently with a frequency slightly lower than the brain wave frequency to be led in a relaxed condition. On the other hand, when a subject intend to be led to a waken state, leading will be accomplished efficiently with a leading frequency slightly higher than the brain wave frequency to be led. Therefore, the equation (1) calculates the leading center frequency F based on such a drawing effect. When the bias frequency $f_b$ is unnecessary, the leading center frequency F becomes only the first term on the right-hand side of the equation (1).

In the next step S2, the time t during which the brain wave has been led is set to t=0. In step S3, the leading of the brain wave starts with the leading center frequency F which have set in the first step S1, and at the same time the weighted mean frequency f' of the brain wave is measured by the brain wave sensor 1.

Then, in step S4 it is determined whether the brain wave leading time t has reached a predetermined time tp as a renewal period. When the leading time t exceeds the predetermined time tp, the next leading center frequency F is obtained for renewal based on the weighted mean frequency measured at time tp, and the flow proceeds to step S6.

If it is necessary for the renewal period tp to be altered in step S6, the flow moves to step S7 in which the renewal period tp is calculated based on the following equation (2) before the flow returns to step S2.

$$tp=tp+t'(t'\neq 0) \quad (2)$$

When the renewal period tp is not necessary to be altered in step S6, the flow returns to step S2.

During the leading of the brain wave, at least the sequence of steps S2 to S6 is repetitively executed. More specifically, the leading center frequency F is renewed every renewal period tp based on the weighted mean frequency f' measured every renewal period tp, and the leading of the brain wave is then continued with this renewed leading center frequency F. Through this renewal process, the leading center frequency F always approaches the weighted mean frequency f' of the brain wave of the subject H, thereby preventing a reduction in brain wave leading efficiency.

Figure 4:
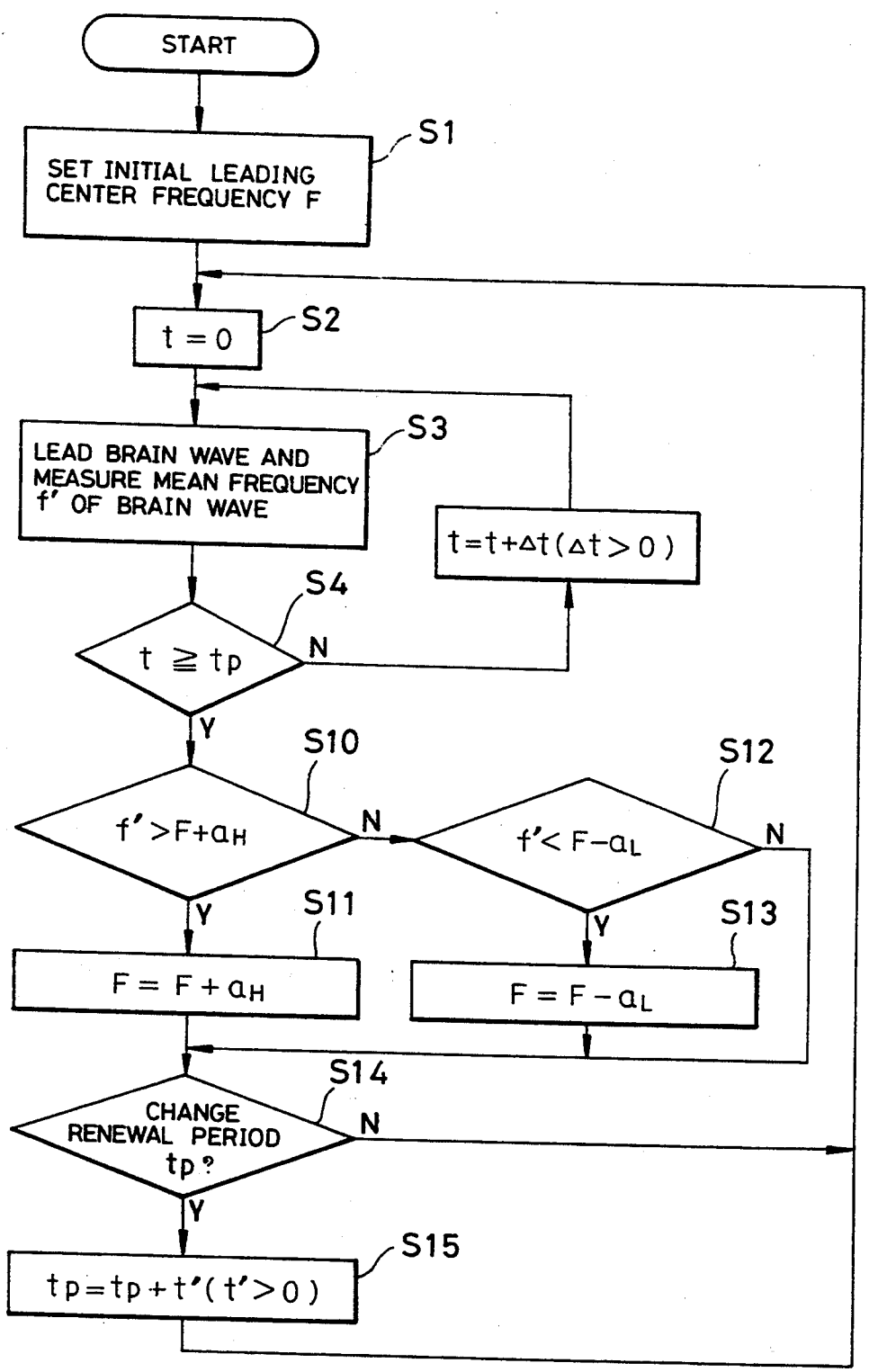
FIG. 4 is a flowchart illustrating the second example of the operation of the brain wave leading apparatus of FIG. 1.

The second operation of the brain wave leading apparatus will be described hereinafter with reference to FIG. 4. In this operation mode, the upper limit and lower limit frequency are preferably defined associated with the leading center frequency F, and the weighted mean frequency f' measured every renewal period is compared with a frequency range between the upper and lower limits of the leading center frequency F to set a subsequent leading center frequency F.

The operation will be specifically described below referring to FIG. 4.

Step 1 through step 4 in this operation are carried out in the same way as those in the above operation of the first example, and step 10 follows the step S4.

In step S10, the weighted mean frequency f' of the brain wave measured every renewal period tp is compared with the upper limit frequency (F+$a_H$). If the weighted mean frequency f' exceeds the upper limit (F+$a_H$) (i.e., f'>F+$a_H$), the flow proceeds to step S11. In step S11, the leading center frequency F is renewed to (F+$a_H$) which is the previous upper limit frequency. The flow then moves to step S14. If the weighted mean frequency f' does not exceed the upper limit frequency (F+$a_H$) (i.e., f'$\leq$F+$a_H$) in step S10, the flow proceeds to step S12.

In step S12, the weighted mean frequency f' is compared with the lower limit frequency (F−$a_L$). If the weighted mean frequency f' is lower than the lower limit (F−$a_L$) (i.e., f'<F−$a_L$), the flow proceeds to step S13. In step S13, the leading center frequency F is renewed to (F−$a_L$) which is the previous lower limit. The flow then moves to step S14. If the weighted mean frequency f' is not lower than the lower limit (F−$a_L$) (i.e., f'$\geq$F−$a_L$) in step S12, the flow proceeds to step S14.

If it is necessary for the renewal period tp to be altered in step S14, the flow moves to step S15 to calculate the renewal period tp based on the equation (2) before the flow returns to step S2, as done in steps S6 and S7 in FIG. 2. If the renewal period tp is not necessary to be altered in step S14, the flow returns directly to step S2.

As described the above, at least the sequence of steps S2 to S4 and step S10, and step S11, step S12 or step S13, which is selected in accordance with the result of the comparison between the weighted mean frequency f' and the leading center frequency F, followed by step S14, is repetitively executed. More specifically, the leading center frequency F is renewed at least every renewal period tp based on the weighted mean frequency f' calculated every renewal period tp, and the leading of the brain wave frequency is then continued with this renewed leading center frequency F.

The upper and lower limit frequency (F+$a_H$) and (F−$a_L$) defined for the leading center frequency F need not be symmetrical to the leading center frequency F, and may be shifted with respect to the leading center frequency F, i.e., $a_H \neq a_L$, due to the drawing effect of brain waves.

Figure 5:
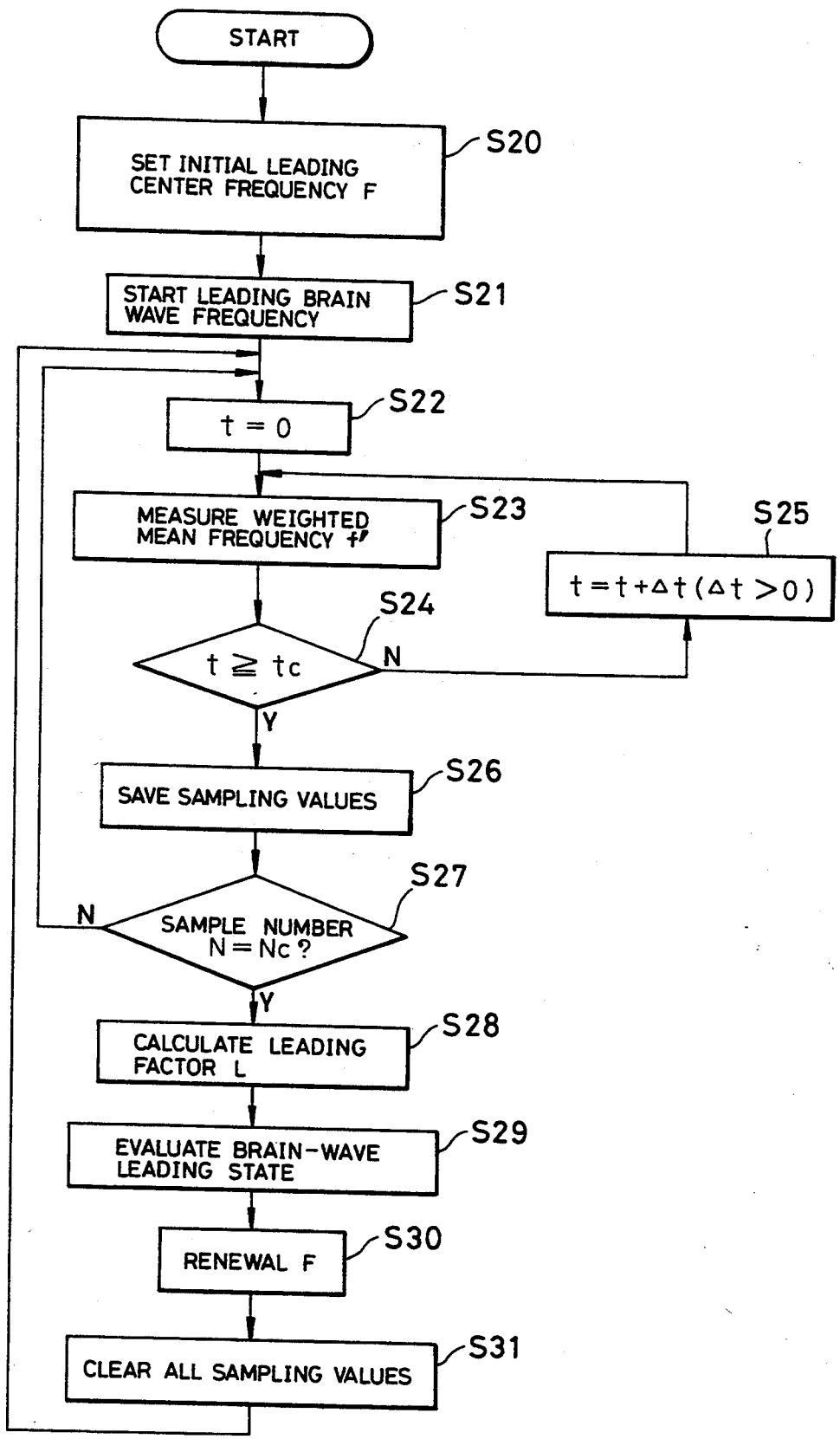
FIG. 5 is a flowchart illustrating the third example of the operation of the brain wave leading apparatus shown in FIG. 1.

The third example of the operation of the brain wave leading apparatus will be described with reference to FIG. 5. In this operation, the brain wave leading status of a subject is evaluated every predetermined interval and the leading center frequency is renewed for the subsequent predetermined interval based on the result of the evaluation. The detailed operation will be discussed below referring to FIG. 5.

In this operational mode, the same process as in step S1 in the each embodiments is performed in step S20 to set the initial leading center frequency F. The brain wave leading with this leading center frequency F starts in the next step S21, and time t is set to t=0 in step S22. In step S23, the weighted mean frequency f' of the subject is measured by the brain wave sensor 1 with leading the brain wave frequency. After the leading time t has passed by a given time tc in step S24, the weighted mean frequency f' of the brain wave of the subject measured at the time tc is saved as one sampling value in the memory of the control means 7. In the next step S27, it is determined if the number of sampling values stored in that memory, N, has reached a predetermined value Nc (Nc≧2). The sequence of steps S23 to S27 will be repeated until the sample number N reaches the predetermined value Nc. When the sample number N has reached the predetermined value Nc in step S27, the flow proceeds to step S28 to evaluate the status of leading the brain wave of the subject.

In this embodiment, a leading factor L as defined by the following equation (3) is introduced to evaluate the brain wave leading status.

$$L = (\text{number of samples included in } <F>) / (\text{total number of samples Nc}) \quad (3)$$

This leading factor L indicates the ratio of the number of the weighted mean frequencies f', all of which are included in a frequency range $<F>$ defined based on the leading center frequency F, to the total sample number Nc. Therefore, the brain wave leading status of the subject is preferably determined from the comparison of the leading factor L with a reference value R. In this case, the reference value R is an evaluation reference factor for determining whether the brain wave leading should be performed, and can be set appropriately. The frequency range $<F>$ may be set using the weighted mean frequency $f_0$ computed at the time the subject is at rest or through a sweeping operation before the brain wave leading, or the current leading center frequency F. Thus, the frequency range $<F>$ preferably differs depending on the subject or the condition of the subject during leading. The range $<F>$ also depends on the final physiological/psychological state to which the brain wave should be led, i.e., whether the subject is in a relaxed or awakening condition.

The leading factor L is calculated in step S28. In the next step S29, the leading factor L is compared with the reference value R to evaluate the leading status of the brain wave. When the leading factor L is equal to or greater than the reference value R, it is determined that the brain wave frequency has been led to a predetermined frequency i.e. the current leading center frequency F. If the leading factor L is smaller than the reference value R, it is determined that the brain wave frequency has not been led to the current leading center frequency F. Then, the leading center frequency F is renewed based on the evaluation of the brain wave leading status in step S30. After all the sample values in the memory are cleared in the next step S31, the flow returns to step S22 to continue the brain wave leading using the renewed leading center frequency F.

The method of renewing the leading center frequency F preferably differs based on the physiological/psychological state of the subject to be led to a desired state.

Figure 6:
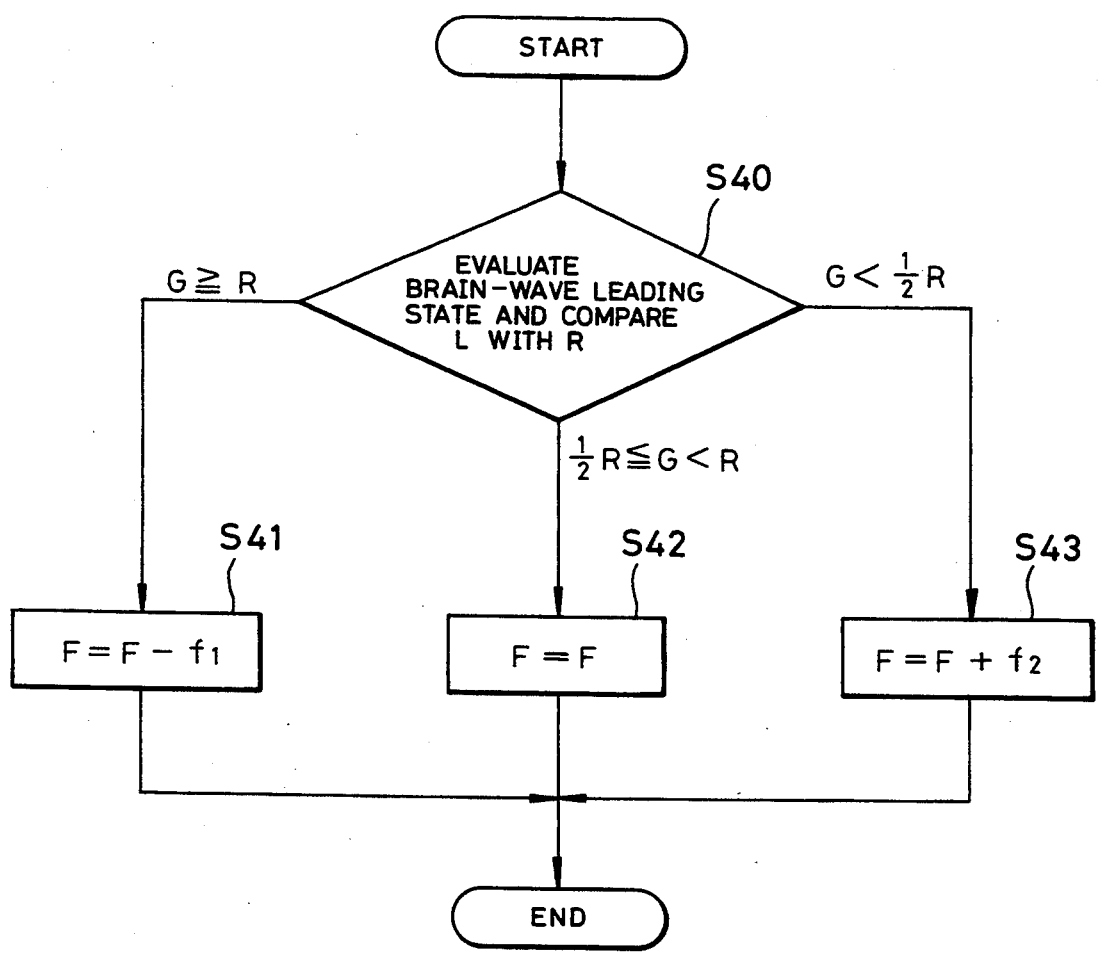
FIG. 6 is a flowchart for explaining a method of renewing a leading center frequency F in the flowchart of FIG. 5.

For instance, in leading the subject mental condition to a relaxed state, as shown in FIG. 6, the leading factor L is compared with the reference value R in step S40. If the leading factor L is found equal to or greater than the reference value R, i.e., if it is determined that the brain wave has been led to the desired frequency range, the leading center frequency F is reduced by frequency level $f_1$ ($f_1 > 0$) to be renewed in step S41. It is to be noted that the frequency level $f_1$ is a properly selected value, and the new leading center frequency F will not become equal to or smaller than a lower limit frequency value defined. If the leading factor L is found less than the reference value R, i.e., if it is determined that the desired brain wave frequency not been triggered in step S40, the leading center frequency F is preferably separated to the following two cases for renewal in accordance with the leading factor L. If the leading factor L is close to the reference value R and preferably satisfies $(\frac{1}{2})R \leq L < R$, the next leading center frequency F is set the same as the current leading center frequency F in step S42. If the leading factor L is far from the reference value R and L is lower than $(\frac{1}{2})R$, the leading center frequency F is increased by a frequency level $f_2$ ($f_2 > 0$) to be renewed in step S43. The $f_2$ is also a properly selected value.

The value with which the leading factor L ($\frac{1}{2}$ in this embodiment) is classified when the leading has not been accomplished is properly selected based on the leading condition. In this operational example, if the leading has not been accomplished, the leading factor L is further classified and the way of renewing the leading center frequency F is changed due to each classified case. This invention is however not limited to this particular case, and the renewing method may be determined specifically.

In leading the subject to a waken state, when the brain wave frequency is led to the current leading center frequency F, the leading center frequency F is increased for renewal to set the next leading center frequency F. If the brain wave frequency is not led to the current leading center frequency F, the leading center frequency F also is used directly as the next leading center frequency F without any change, or the leading center frequency F is decreased, depending on how far apart the brain wave frequency is from the desired leading center frequency F.

In this operation example, the brain wave leading state is evaluated every predetermined interval and the leading center frequency F is renewed based on the evaluation.

In any operational example of the brain wave leading apparatus described above, the intensity of the biostimulation signal that is supplied to a subject need not be even over the entire process from the beginning of the leading to the end thereof, and may be varied in accordance with the state of the subject during leading and the final desired physiological/psychological state of the subject.

For instance, the luminance of light or the volume of a sound, as the biostimulation signal, may be altered in accordance with the renewal of the leading center frequency F. In this case, when the leading center frequency F is decreased for renewal, the luminance is reduced and the volume is lowered. When the leading center frequency F is increased for renewal, on the other hand, the luminance is increased and the volume is increased.

The luminance of light or the volume of a sound may be gradually increased from the beginning of the leading, and may be gradually decreased and the leading is terminated.

In each of the brain wave leading apparatus of the above-described embodiments, in leading the brain wave of a subject, the leading center frequency F is renewed based on the current brain wave frequency of the subject so that the leading center frequency F will approach the current weighted mean frequency f' of the subject during leading. Therefore, the entraining phenomenon of the brain wave occurs efficiently, thus improving the brain wave frequency leading efficiency. That is, fine leading based on the current brain wave frequency of the subject can be executed during leading.

Although the initial leading center frequency at the beginning of leading in steps S1 and S20 is set based on the result of the brain wave sweeping operation carried out before the leading, this invention is not limited to this particular case. For example, the weighted mean frequency of the brain wave of the subject in a relaxed condition may be set as the leading center frequency F at the beginning of the leading, or may be defined by some other proper means.

Although the weighted mean frequency $f_0$ of the brain wave of the subject is continuously measured during leading, this weighted mean frequency $f_0$ may be measured only when necessary, such as every predetermined interval tp and every predetermined interval tc.

Figure 7:
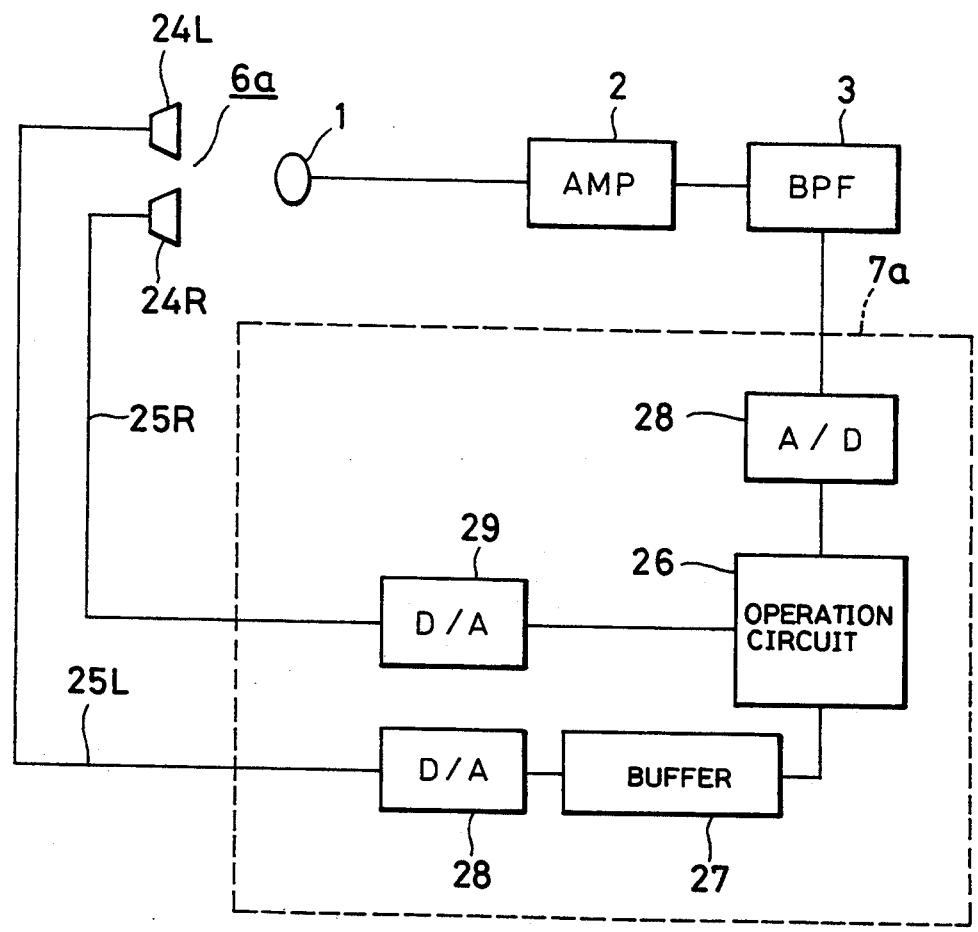
FIG. 7 is a diagram showing another embodiment of brain wave leading apparatus according to the present invention.

FIG. 7 shows a brain wave leading apparatus having a different structure from that of the apparatus of FIG. 1. This apparatus comprises a brain wave sensor 1 such as electrodes to be attached to predetermined positions of the head of a subject H, a bioamplifier 2, a bandpass filter 3, control means 7a and light emitting means 6a all connected in the named order.

The brain wave sensor 1, bioamplifier 2 and bandpass filter 3 are the same as those of FIG. 1.

Figure 8:
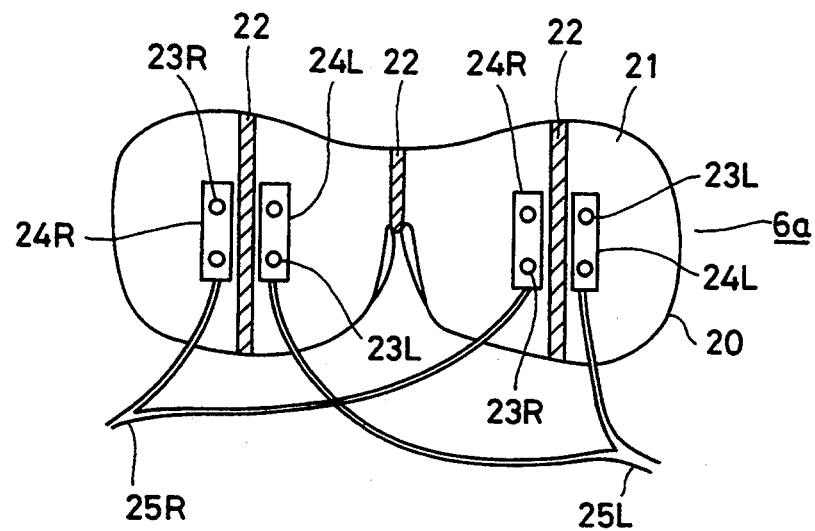
FIG. 8 is a front view of a goggle shown as light emitting means of the brain wave leading apparatus of FIG. 7.

The light emitting means 6a includes a goggle 20 whose body is attachable to the subject, as shown in FIG. 8. Attached nearly vertical to a cover portion 21 for covering the face of the subject are partitions 22 which extend vertically at positions respectively opposite to the centers of the each eyeballs that will come in front. Those partitions 22 separate the field of view of each eyeball of the subject H to the right field of view and the left field of view, which are biologically classified. Pairs of right-view-field and left-view-field light emitting portions 24R and 24L, which respectively include light emitting diodes (LEDs) 23R and 23L, are further provided on the cover portion 21, with each partition 22 in between each pair. The flickering lights emitted from the LEDs 23R and 23L are irradiated on the right and left fields of view of the subject as optical biostimulation signals respectively for leading the brain wave of the subject into a desired frequency range. Of those light emitting portions, the right-view-field and the left-view-field light emitting portions 24R and 24L are electrically connected as same lead wires 25R to an associated one of the two output terminals of the control means 7a, while the left-view-field light emitting portions 24L are electrically connected as same lead wires 25L to the other output terminal of the control means 7a. The LEDs 23R and 23L of the each light emitting portions 24R and 24L are blinked by the control means 7a respectively.

The light emitting means 6a is constituted in such a way that the optical biostimulation signal emitted from the right-view-field light emitting portion 24R will not leak through the partition 22 into the goggle area which is controlled by the left-view-field light emitting portion 24L for the same eyeball. That is, only the optical biostimulation signal emitted from the right-view-field light emitting portion 24R is irradiated in the right field of view of each eyeball, and only the optical biostimulation signal emitted from the left-view-field light emitting portion 24L is irradiated in the left field of view of each eyeball.

The control means 7a is preferably constituted of a microcomputer, and includes an operation circuit 26 for supplying two drive signals to drive the light emitting means 6a based on the detected brain wave signal and a buffer 27 corresponding to a delay circuit for delaying the timing of one of the drive signals. The control means 7a further includes an A/D converter 28 for converting an analog signal to a digital signal and a D/A converter for converting a digital signal to an analog signal.

Figure 9A:
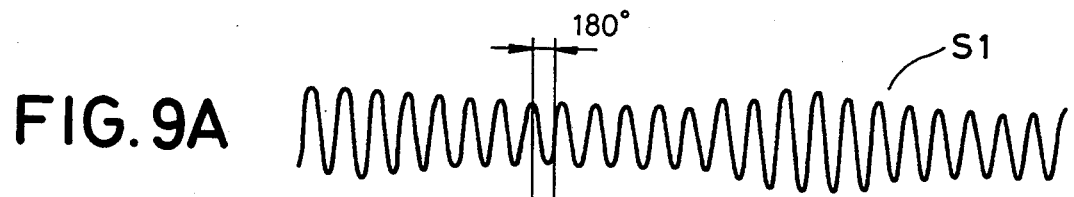
FIGS. 9A and 9B show a first and second optical stimulation signals to be supplied to a light emitting portion of the light emitting means for the right and left field of views, respectively.
Figure 9B:
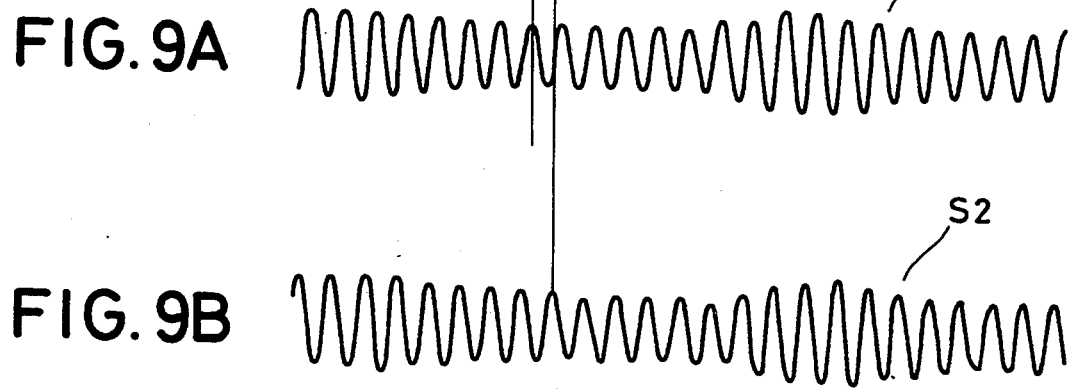
Figure 10:
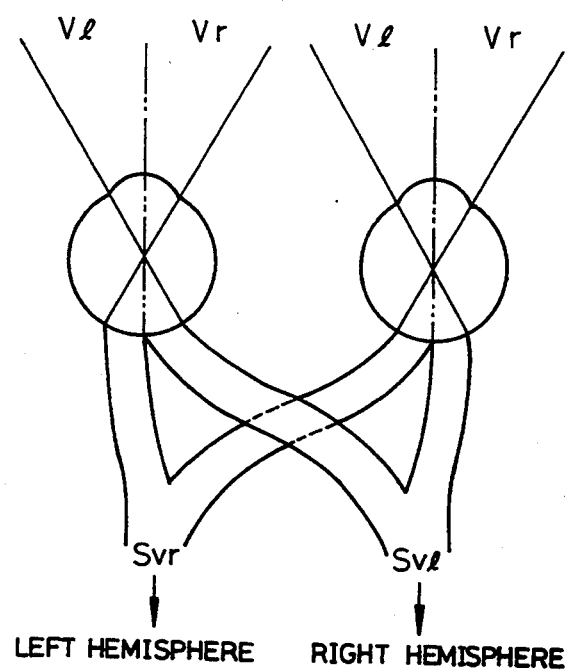
FIG. 10 is a model diagram for explaining the transmission of optical stimulation signals to the hemispheres of the subject by the brain wave leading apparatus of FIG. 7.

The operation of this brain wave leading apparatus, when used to lead an α wave in the brain of a subject, for example, will be described below with reference to FIGS. 9A, 9B and 10.

To fix the eyeballs of a subject to predetermined positions, the subject's viewing direction is set in due front by instructing the subject to close the eyes unconsciously and naturally or by some other means. Then, when a switch (not shown) on the apparatus is turned on, the brain wave sensor 1 starts detecting the brain wave signal of the subject and sends it to the bioamplifier 2. This brain wave signal is amplified by the bioamplifier 2. The amplified brain wave signal is then sent to the bandpass filter 3 in which only the frequency component around 10 Hz, which corresponds to the desired α wave, is selected and the output signal of bandpass filter 3 is sent to the control means 7a.

Based on the output signal of the bandpass filter 3, the operation circuit 26 in the control means 7a produces two drive signals to drive the light emitting means 6a. One of the drive signals is supplied as a first optical stimulation signal to the right-view-field light emitting portions 24R for the right and left eyeballs via the D/A converter 29. The other drive signal is temporarily stored in the buffer 27 to delay its timing so that this drive signal has a phase difference with respect to the first optical stimulation signal. The delayed signal is then supplied as a second optical stimulation signal to the left-view-field light emitting portions 24L for the right and left eyeballs via the D/A converter 29. The first and second optical stimulation signals are exemplified in FIG. 3 in which the phase difference between both signals is set to about 180 degrees. The LEDs 23R and 23L in the light emitting portions 24R and 24L are blinked based on the supplied optical stimulation signals respectively, and the flickering lights of the LEDs 23R and 23L are irradiated on the respective fields of view of the eyeballs respectively, stimulating them.

In general, each eyeball of a human being is separated into the right field of view Vr and a left field view Vl, and each field of view is inverted inside the eyeball so that a visual signal $S_{Vr}$ of the right field of view Vr of each eyeball is transmitted to the left hemisphere and a visual signal $S_{vl}$ of the left field of view Vl of each eyeball is transmitted to the right hemisphere.

The supply of optical stimulation signals of different phases to the right and left hemispheres via the right and left fields of view Vr and Vl causes a drawing phenomenon on the right and left hemispheres so that the right and left hemispheres can be activated independently. The separate activation of the right hemisphere and the left hemisphere will further improve information exchange between the right and left hemispheres. In this manner, the brain wave can be led to the desired frequency band, while improving information exchange between the right and left hemispheres.

Changing the phase difference between the first and second optical stimulation signals S1 and S2 can permit the adjustment of the method of activating the right and left hemispheres.

Figure 11:
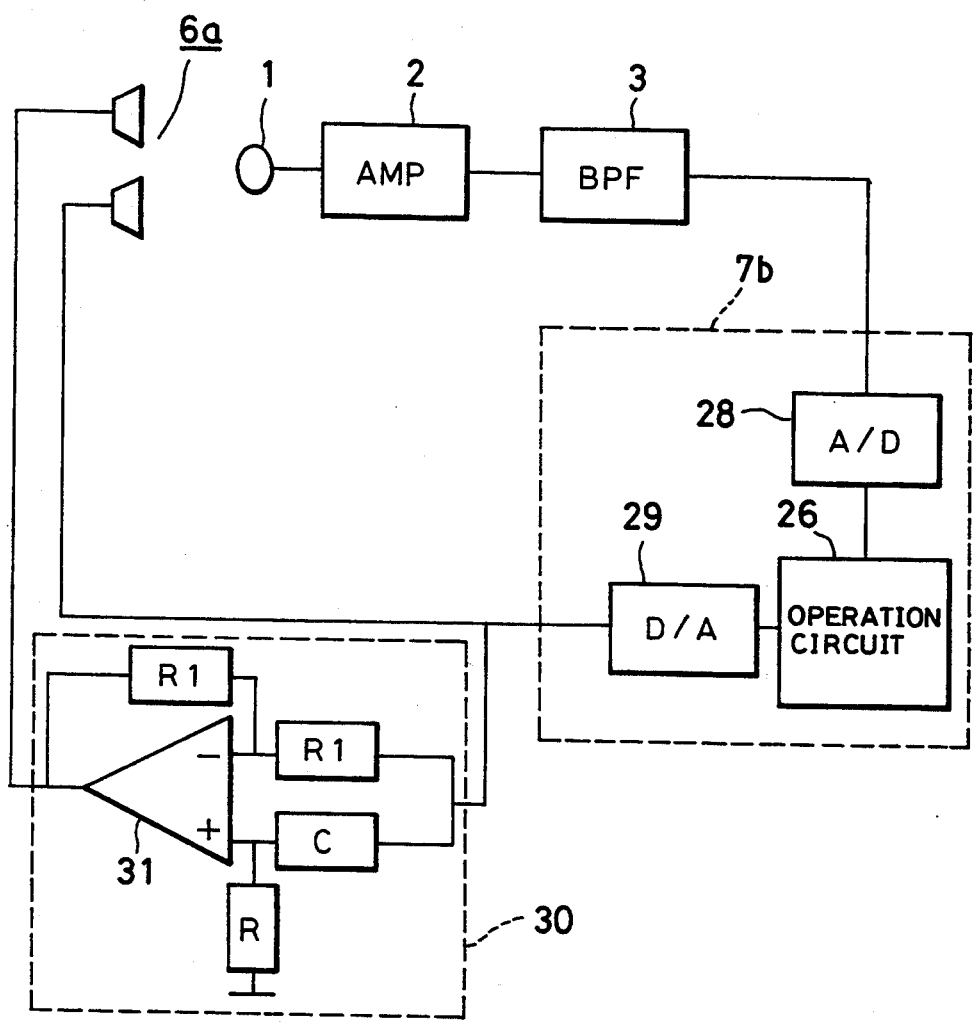
FIG. 11 is a diagram showing the structure of a brain wave leading apparatus different from that of the brain wave leading apparatus of FIG. 7.

FIG. 11 shows a brain wave leading apparatus having a different structure from that of the apparatus of FIG. 7. The brain wave leading apparatus of FIG. 11 has almost the same structure as the apparatus shown in FIG. 7, so that the same reference numerals as used for the components of the latter apparatus of FIG. 7 will be given to denote identical or corresponding components in FIG. 11 to thereby avoid repeating their description.

Control means 7b includes an operation circuit for producing drive signals to drive light emitting means 6a based on the detected brain wave signal.

The assembly of the light emitting means 6a is constituted in the same way as that of the previous embodiment, except for the right-view-field light emitting portions 24R connected directly to the output terminal of the control means 7b. The left-view-field light emitting portions 24L are connected to the output terminal of the control means 7b via an analog delay circuit 30. The left-view-field light emitting portions 24L may be connected directly to the output terminal of the control means 7b, while the right-view-field light emitting portions 24R may be connected to the output terminal of the control means 7b via the analog delay circuit 30.

The analog delay circuit 30 comprises resistors R1, R1 and R, a capacitor C and an operational amplifier 31, and delays the input signal by a desired time.

The operation of this brain wave leading apparatus for leading an $\alpha$ wave will be described below.

When a switch (not shown) on this apparatus is turned on, the brain wave signal of the subject detected by the brain wave sensor 1 is sent to the bioamplifier 2 to be amplified, and only the frequency component of the amplified signal around 10 Hz, which corresponds to the desired $\alpha$ wave, is selected by the bandpass filter 3 and is then sent to the control means 7b as in the case of the apparatus shown in FIG. 7.

Based on the output signal of the bandpass filter 3, the operation circuit 26 in the control means 7b produces drive signals to drive the light emitting means 6a. One of the drive signals is supplied as a first optical stimulation signal directly to the right-view-field light emitting portions 24R. At the same time, the other output signal of the control means 7b is supplied into the analog delay circuit 30 to be delayed there, so that this drive signal has a phase difference with respect to the first optical stimulation signal. The delayed signal is then supplied as a second optical stimulation signal to the left-view-field light emitting portions 24L. The LEDs 23R and 23L in the light emitting portions 24R and 24L are blinked by the supplied optical stimulation signals respectively, and the flickering lights of the LEDs 23R and 23L are irradiated on the respective fields of view of the eyeballs, stimulating those fields of view.

It should be understood from the above description that the right and left hemispheres can be activated independently as per the previous embodiment, thus further improving information exchange between the right and left hemispheres.

Although the foregoing description of the above embodiments has been given with reference to the case of leading an $\alpha$ wave, this invention is not limited to the above-described embodiments but may be adapted to lead a theta wave and a beta wave as well without sacrificing the advantages of the above-described embodiments. For instance, the sweep frequency range should be set to 4 to 7 Hz corresponding to the theta wave band to trigger a theta wave, and should be set to 14 to 30 Hz corresponding to a beta wave band to induce the beta wave in the brain of the subject.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A brain wave leading apparatus for leading a brain wave frequency of a person to be tested to a desired frequency band, comprising:
   detection means for detecting a brain wave frequency of said person;
   filtering means having a passband for passing a desired brain wave signal from the brain wave frequencies detected by the detection means; and
   signal supplying means for generating a biostimulation signal to be supplied to the person according to the brain wave signal wherein said passband is renewed in accordance with the brain wave frequencies detected by said detection means at a predetermined time interval during the leading of the brain wave frequency band.

2. The brain wave leading apparatus according to claim 1, further comprising calculating means for calculating a weighted mean frequency of the brain wave detected by the detection means at a predetermined time interval during the leading.

3. The brain wave leading apparatus according to claim 2, wherein the weighted mean frequency of the brainwave over the latest time interval defines a passband of said filtering means in the following time interval.

4. The brain wave leading apparatus according to claim 2, further comprising means for determining whether or not the weighted mean frequency detected in the latest predetermined interval is included in a predetermined frequency band which is limited by the desired frequency band, whereby if it is determined that the weighted mean frequency is included in said predetermined frequency band, the passband of the filtering means in the following time interval is set to be the same as the passband of the latest time interval, and if it is determined that said weighted mean frequency is out of said predetermined frequency band, the passband of the filtering means in the following time interval is altered in view of the latest weighted mean frequency.

5. The brain wave leading apparatus according to claim 1 or 2, further comprising evaluation means for evaluating a leading status of a brain wave frequency detected in the latest predetermined time interval by the detection means, whereby a result of comparison of an output of said evaluation means with a reference value defines the passband of the filtering means in the following time interval.

6. The brain wave leading apparatus according to claim 1, wherein said biostimulation signal is flickering light.

7. The brain wave leading apparatus according to claim 6, further comprising:
 a goggle having two cover portions, each cover portion covering respective eyes of the subject and including a first and second partition extending vertically and centered respectively over each eye, each of said partitions respectively separating the right field of view and the left field of view, wherein two pairs of right view field and left view field light emitting portions are respectively located on the cover portions on either side of each said partition, said right view field and left view field light emitting portions each including light emitting devices, said flickering lights emitted from said light emitting devices being irradiated on the right and left fields of view of the subject as optical biostimulation signals, and said goggles being constituted such that the biostimulation signal emitted from the right view field light emitting portion will not leak through said partition into the goggle area controlled by the left view field light emitting portion for the same eye.

8. The brain wave leading apparatus according to claim 1, wherein said biostimulation signal is a sound.

* * * * *